(12) United States Patent
Podgorsak et al.

(10) Patent No.: US 11,167,151 B2
(45) Date of Patent: Nov. 9, 2021

(54) METHOD AND SYSTEM FOR TRANSFERRING RADIATION THERAPY TREATMENT PLANS FROM A HIGH DEFINITION MLC TO A LOWER DEFINITION MLC

(71) Applicant: Health Research, Inc., Buffalo, NY (US)

(72) Inventors: Matthew Podgorsak, Williamsville, NY (US); Daryl Nazareth, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 146 days.

(21) Appl. No.: 16/613,993

(22) PCT Filed: May 16, 2018

(86) PCT No.: PCT/US2018/032946
§ 371 (c)(1),
(2) Date: Nov. 15, 2019

(87) PCT Pub. No.: WO2018/213431
PCT Pub. Date: Nov. 22, 2018

(65) Prior Publication Data
US 2020/0078604 A1    Mar. 12, 2020

Related U.S. Application Data

(60) Provisional application No. 62/506,764, filed on May 16, 2017.

(51) Int. Cl.
*A61N 5/10*    (2006.01)

(52) U.S. Cl.
CPC .......... *A61N 5/103* (2013.01); *A61N 5/1045* (2013.01); *A61N 2005/1074* (2013.01)

(58) Field of Classification Search
None
See application file for complete search history.

(56) References Cited

U.S. PATENT DOCUMENTS 6,335,961 B1    1/2002  Wofford et al.
2014/0239204 A1    8/2014  Orton et al.
(Continued)

OTHER PUBLICATIONS

Men, C., et al., Ultrafast treatment plan optimization for volumetric modulated arc therapy (VMAT), Medical Physics, Oct. 14, 2010, vol. 37, No. 11, 16 pages.
(Continued)

*Primary Examiner* — Hoon K Song
(74) *Attorney, Agent, or Firm* — Hodgson Russ LLP (57) ABSTRACT

Linear accelerator ("linac") downtime invariably impacts delivery of patients' scheduled treatments. Transferring a patient's treatment to an available linac is a common practice. Transferring a VMAT plan from a linac equipped with a standard-definition MLC to one equipped with a higher definition MLC is practical and routine in clinics with multiple MLC-equipped linacs. However, the reverse transfer presents a challenge because the high-definition MLC aperture shapes must be adapted for delivery with the lower definition device. An efficient method to adapt VMAT plans originally designed for a high-definition MLC to a standard definition MLC is disclosed herein. The dosimetric results of the present adaptation method are presented for head-and-neck, brain, lung and prostate VMAT plans. The delivery of the adapted plans was verified using standard phantom measurements.

13 Claims, 8 Drawing Sheets

(56) References Cited

U.S. PATENT DOCUMENTS

| | | |
|---|---|---|
| 2014/0378736 A1 | 12/2014 | Fox et al. |
| 2017/0157423 A1* | 6/2017 | Bokrantz .............. A61N 5/1045 |
| 2019/0030372 A1* | 1/2019 | MacDonald ........... A61N 5/103 |
| 2019/0054320 A1* | 2/2019 | Owens ................. A61N 5/1071 |
| 2019/0192880 A1* | 6/2019 | Hibbard ............... A61N 5/1039 |

OTHER PUBLICATIONS

Yin, L., et al., Volumetric-modulated arc therapy vs c-IMRT in esophageal cancer: A treatment planning comparison, World Journal of Gastroenterology, Oct. 7, 2012, vol. 18, No. 37, pp. 5266-5275.

* cited by examiner

Fig. 1

Table 1

| Treatment site | Structure | Percent Difference (mean ± st. dev.) |
|---|---|---|
| Brain | Brainstem Mean | 4.1 ± 5.3 |
| | Brainstem Max | 7.0 ± 9.1 |
| | Lens L Mean | 7.3 ± 8.7 |
| | Lens L Max | 8.8 ± 10.9 |
| | Lens R Mean | 6.6 ± 9.5 |
| | Lens R Max | 6.1 ± 13.5 |
| | Optic Nerve L Mean | 4.0 ± 4.8 |
| | Optic Nerve L Max | 4.1 ± 4.8 |
| | Optic Nerve R Mean | 5.1 ± 16.3 |
| | Optic Nerve R Max | 7.1 ± 18.4 |
| | Target Mean | 2.9 ± 2.3 |
| | Target Max | 8.1 ± 3.7 |
| Head & Neck | Brainstem Mean | -2.7 ± 3.1 |
| | Brainstem Max | 1.2 ± 3.0 |
| | Parotid L Mean | -0.7 ± 2.2 |
| | Parotid L Max | -0.9 ± 4.7 |
| | Parotid R Mean | -0.1 ± 2.2 |
| | Parotid R Max | -1.1 ± 4.8 |
| | Spinal Cord Mean | 2.1 ± 3.7 |
| | Spinal Cord Max | 5.8 ± 5.5 |
| | Target Mean | 3.4 ± 2.4 |
| | Target Max | 8.9 ± 4.9 |
| Lung | Lung Mean | -6.2 ± 3.6 |
| | Lung Max | 1.0 ± 20.2 |
| | Spinal Cord Mean | -8.3 ± 4.3 |
| | Spinal Cord Max | -9.7 ± 3.3 |
| | Target Mean | -5.1 ± 4.2 |
| | Target Max | 3.9 ± 5.4 |
| Prostate | Bladder Mean | 1.8 ± 5.2 |
| | Bladder Max | 7.1 ± 5.8 |
| | Rectum Mean | 1.8 ± 4.0 |
| | Rectum Max | 3.6 ± 3.4 |
| | Fem Head L Mean | -1.2 ± 3.6 |
| | Fem Head L Max | 0.2 ± 4.7 |
| | Fem Head R Mean | -0.8 ± 3.5 |
| | Fem Head R Max | 0.3 ± 5.0 |
| | Target Mean | -0.2 ± 3.6 |
| | Target Max | 8.0 ± 5.7 |

Fig. 5

Table 2

| Treatment site | Structure | Percent Difference (mean ± st. dev.) |
|---|---|---|
| Brain | Target HD Plan | 0.13 ± 0.11 |
| | Target Adapted | 0.25 ± 0.09 |
| Head & Neck | Target HD Plan | 0.10 ± 0.3 |
| | Target Adapted | 0.21 ± 0.07 |
| Lung | Target HD Plan | 0.11 ± 0.02 |
| | Target Adapted | 0.27 ± 0.08 |
| Prostate | Target HD Plan | 0.11 ± 0.02 |
| | Target Adapted | 0.26 ± 0.05 |

Fig. 6

Table 3

| | Brain | H&N | Lung | Prostate | TOTAL |
|---|---|---|---|---|---|
| Distance to Agreement, percent passing (3%/3mm) | 98.0±2.1 | 98.5±1.1 | 98.2±0.9 | 98.9±0.6 | 98.4±1.4 |

METHOD AND SYSTEM FOR TRANSFERRING RADIATION THERAPY TREATMENT PLANS FROM A HIGH DEFINITION MLC TO A LOWER DEFINITION MLC

CROSS-REFERENCE TO RELATED APPLICATIONS

This application is a National Phase of International Patent Application No. PCT/US2018/032946, filed on May 16, 2018, which claims priority to U.S. Provisional Application No. 62/506,764, filed on May 16, 2017, the disclosures of which are incorporated herein by reference.

FIELD OF THE DISCLOSURE

The present disclosure relates to radiotherapy treatment planning systems.

BACKGROUND OF THE DISCLOSURE

Typically, a patient's entire radiotherapy treatment course is delivered in sequential daily fractions (weekends excepted) on a particular linear accelerator ("linac") for which the radiation plan was designed. However, linac malfunction occasionally causes downtime, and may require the transfer of patient plans between linacs. In an exemplary department, one linac is equipped with a Varian high-definition multileaf collimator ("MLC") (HD120), while multiple linacs have standard-definition Millennium MLCs (Millennium 120). Such linacs are commissioned to deliver volumetric modulated arc therapy ("VMAT") treatments. In addition to differences in leaf widths, different MLCs may differ in material composition and geometric properties (leaf thickness, tongue-and-groove design, and leaf-end curvature), which creates dosimetric differences between VMAT plans. Nevertheless, the single-fraction transfer of a treatment may be desirable to maintain the prescribed fractionation schedule. Fractionation plays a sensitive and demonstrable role in patient outcomes for head-and-neck treatments, and likely for other treatment sites.

A previous study investigated transferring patients between linacs using a Pinnacle/Aria-based treatment planning system ("TPS"). Transferring a VMAT plan was not possible without re-optimization. There is a long-felt need for a way to transfer patients between linacs to accommodate linac unavailability.

BRIEF SUMMARY OF THE DISCLOSURE

According to an embodiment of the present method, a high-definition VMAT plan (from a high-definition linac—an "HDL") can be adapted to a standard-definition linac ("SDL") by creating a new plan (the "adapted" plan) using the DICOM plan file. The resulting adapted plan is analyzed within the TPS and exported to a record-and-verify system for treatment delivery.

DESCRIPTION OF THE DRAWINGS

For a fuller understanding of the nature and objects of the disclosure, reference should be made to the following detailed description taken in conjunction with the accompanying drawings, in which:

FIG. 2 depicts a method for adaptation of leaves according to the present disclosure, wherein high-definition leaves are averaged and assigned to single standard-definition leaves and leaves of similar width are mapped directly;

FIG. 3 depicts images from a treatment planning system ("TPS") for a VMAT control point, wherein an HDL aperture is on the left; and an SDL adaptation for the same control point is on the right;

FIG. 4A-4D are charts showing the mean percent difference in target doses between the original HDL and the plans adapted to the SDL for (FIG. 4A) brain, (FIG. 4B) head-and-neck, (FIG. 4C) lung, and (FIG. 4D) prostate;

DETAILED DESCRIPTION OF THE DISCLOSURE

The present disclosure may be embodied as a computer-implemented method of adapting a volumetric modulated arc therapy ("VMAT") plan for a linear accelerator ("linac") having a high-definition multileaf collimator ("HDL MLC") for use with a linac having a standard-definition ("SDL MLC"). Multileaf collimators used with linacs are known to have a plurality of leaves, where each leaf is operable such that a leaf aperture shape can be defined. In an exemplary high-definition MLC configurations, the MLC leaves have a 14-32-14 pattern of widths 0.5-0.25-0.5 cm, respectively (i.e., 14 leaves of width 0.5 cm, 32 leaves of width 0.25 cm, and 14 leaves of width 0.5 cm). The leaves of an exemplary standard-definition collimator have a 10-40-10 pattern of widths 1.0-0.5-1.0 cm, respectively. Transferring a VMAT plan from a linac equipped with a standard-definition MLC to one equipped with a higher definition MLC is practical and routine in clinics with multiple MLC-equipped linacs. However, the reverse transfer presents a challenge because the high-definition MLC aperture shapes must be adapted for delivery with the lower definition device.

Figure 12:
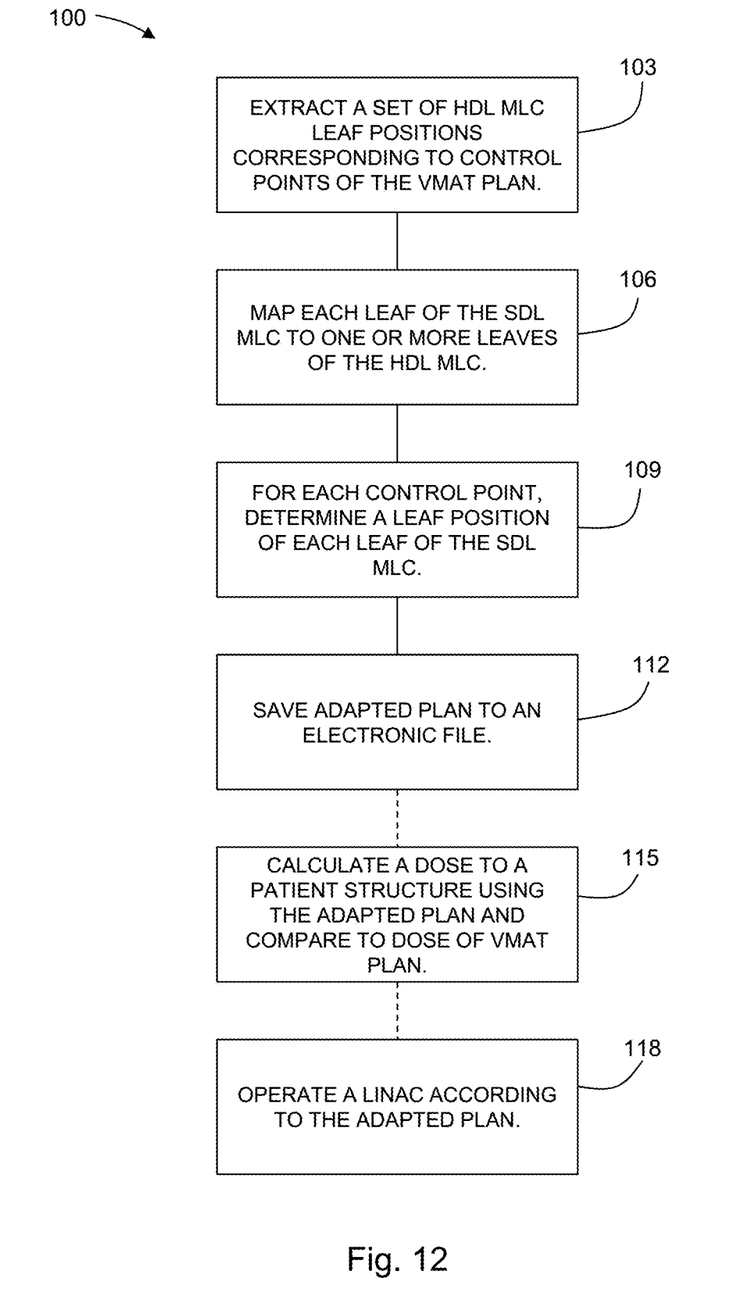
FIG. 12 is a flowchart showing a method according to an embodiment of the present disclosure.

With reference to FIG. 12, the present disclosure may be embodied as a method 100 of adapting a VMAT plan for a linac having an HDL MLC, to a plan for use with a linac having an SDL MLC. The method 100 comprises extracting 103 a set of HDL MLC leaf positions corresponding to a set of control points of the VMAT plan from an HDL DICOM file. For example, an HDL DICOM file may include leaf aperture shapes, field weights and control point monitor unit ("MU") indices. Each leaf of the plurality of leaves of the SDL MLC is mapped 106 to one or more leaves of a plurality of leaves of the HDL MLC according to a width of each leaf of the SDL MLC and HDL MLC. For each control point of the VMAT plan, a leaf position of each leaf of the SDL MLC is determined 109 based on an average leaf position of the corresponding mapped one or more leaves of the HDL MLC to create an adapted plan (i.e., the high-definition VMAT plan adapted for use with the standard definition MLC). For example, FIG. 2 shows where leaf positions $x_1$ and $x_2$ of two 0.25 cm leaves of an HDL MLC are averaged to determine the leaf position, $x_{average}$ of the corresponding 0.5 cm leaf of an SDL MLC. In the original VMAT plan, the velocity of each leaf during movement between adjacent control points has already been constrained by the TPS not to violate the maximum velocity constraints of the system. The averaging process ensures that, by the triangle inequality, the velocity of each leaf of the SDL MLC will automatically obey these constraints as well. The adapted plan is saved 112 to an electronic file, for example, in the industry-standard DICOM format.

The method 100 may further comprise calculating 115 a dose to a patient structure using the adapted plan and comparing the calculated dose to a dose delivered to the patient structure using the VMAT plan. The dose(s) may be calculated using the dosimetry tools of a treatment planning system ("TPS"). The calculated dose may comprise calculating a dose over a period of time over one or more control points (VMAT arcs). In this way, the difference(s) between the dose delivered by the adapted plan and the dose delivered by the (original) VMAT plan may be determined. The difference may be determined as a percentage difference. A homogeneity index, HI, may be calculated based on the determined dosage difference(s). In this way, the patient dosage using the adapted plan can be compared to the original VMAT plan to determine if further review of the adapted plan is required. For example, a pre-determined threshold may be set such that dosage differences exceeding the threshold require further review and/or modification.

The method 100 may include operating 118 a linac according to the adapted plan. In particular, a standard-definition MLC of a linac may be operated through one or more control points, and the leaves of the MLC may form leaf apertures according to the adapted plan.

Figure 13:
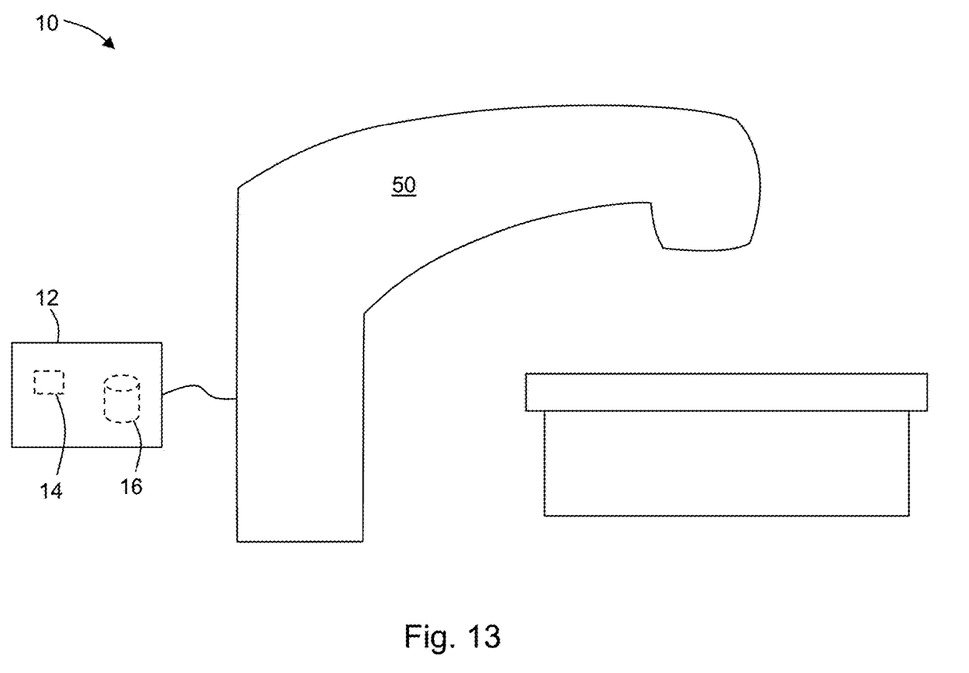
FIG. 13 is a diagram showing a system according to another embodiment of the present disclosure.

In another embodiment, processor-executable software instructions are stored on a non-transitory computer-readable storage medium. The instructions are configured to cause a processor to perform operations comprising any of the methods disclosed herein. For example, the storage medium may have instructions configured to cause a processor to extract a set of HDL MLC leaf positions corresponding to a set of control points of a VMAT plan from an HDL DICOM file; map each leaf of a plurality of leaves of an SDL MLC to one or more leaves of a plurality of leaves of an HDL MLC according to a width of each leaf of the SDL MLC and HDL MLC; determine a leaf position of each leaf of the SDL MLC based on an average leaf position(s) of the corresponding mapped leaves of the HDL MLC to create an adapted plan; and save the adapted plan to an electronic file in DICOM format With reference to FIG. 13, the present disclosure may be embodied as a system 10 for operating a linac 50. The system 10 may comprise a processor 12 and an electronic storage device 14 in communication with the processor 12. The system 10 further comprises a linac 50 having a standard-definition MLC. The processor 12 is programmed to perform a method according to any of the embodiments disclosed herein. It should be recognized that the processor 12 may be made up of more than one processor and each processor may perform one or more of the steps of the disclosed methods. For example, a processor may be programmed to generate an adapted plan, while another processor is programmed to operate the linac 50 according to the generated adapted plan.

Furthermore, although described as a processor, it is to be appreciated that the processor(s) may be implemented in practice by any combination of hardware, software, and/or firmware. Also, its functions as described herein may be performed by one unit, or divided up among different components, each of which may be implemented in turn by any combination of hardware, software and firmware. Program code or instructions for the processor to implement the various methods and functions described herein may be stored in processor-readable storage media, such as memory (e.g., electronic storage device).

The methods of the present disclosure are further described with respect to the exemplary methods below, some of which were implemented in an exemplary clinic as will be apparent in light of the disclosure. The exemplary methods and clinic are used herein to further illustrate embodiments of the present disclosure, and are not intended to be limiting.

Exemplary Methods

A MATLAB routine was written to take data related to the delivery of volumetric modulated arc therapy ("VMAT") (leaf aperture shapes, field weights and control point monitor unit ("MU") indices) contained in the planning DICOM file and place it into a prepared template, that is, a VMAT plan prepared inside a treatment planning system ("TPS") for a standard-definition linac ("SDL") to which the patient would be transferred. This template is created by making a copy of the original high-definition linac ("HDL") plan and modifying it. The MATLAB code operates on exported copies of the original HDL plan and the SDL template. The VMAT plan information is extracted from the HDL DICOM into the MATLAB workspace, and the leaf shapes are averaged, or mapped one-to-one, to corresponding leaves in the SDL MLC, creating the adapted plan. The adapted plan is saved in the DICOM format and imported into the TPS where the full complement of dosimetry tools is available, e.g., dose calculators, dose volume histogram ("DVH") displays, and plan summing. After dose calculation, each studied patient plan was compared between its original version and the adapted version where the prescription of the original plan was preserved, e.g., 100% Rx dose to 95% of the target volume.

MLCs and DICOM File Creation

Eclipse version 13.6 (Varian Inc., Palo Alto, Calif.) was used as an exemplary TPS for a study. A copy of the original HDL plan was created in Eclipse and the linac was changed from an HDL to an SDL in the plan properties. This process automatically removes the dynamic MLC positions defining the control point apertures stored in the plan. A new MLC object was then added to each field (VMAT arc) in the SDL plan, and the number of control points was set by the user to match the original number found in the HDL fields. The TPS template method provides the entire beam modelling data required to calculate dose correctly for the SDL.

Leaf Adaptation: Mapping and Averaging

Figure 1:
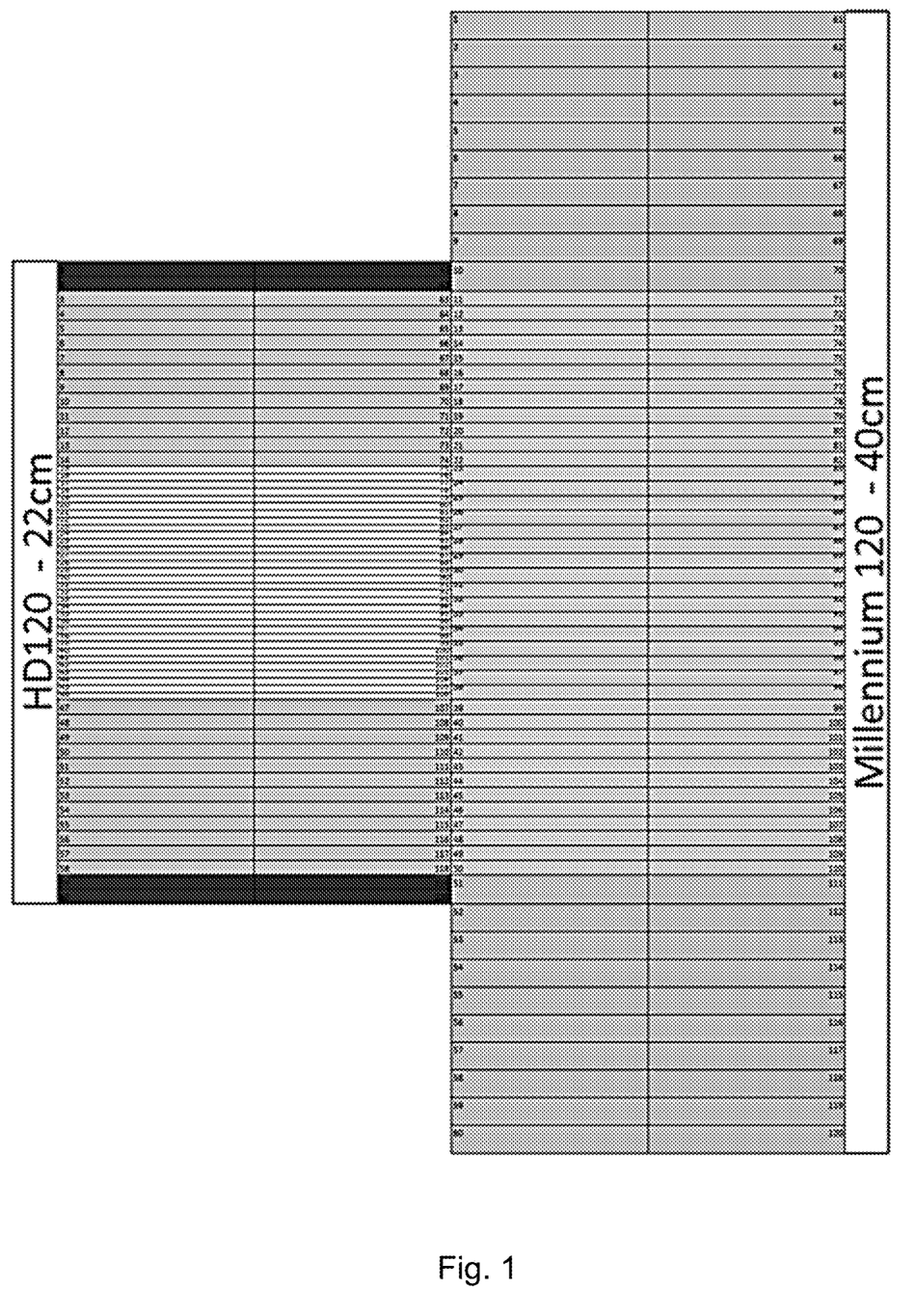
FIG. 1 is an illustration comparing the relative leaf widths and locations of the leaves between an exemplary high-definition multileaf collimator ("MLC") (an HD120 MLC) and an exemplary standard-definition MLC (a Millennium MLC 120)

Both the HDL and SDL MLCs have 120 leaves (60 per bank). The HDL leaves have a 14-32-14 pattern of widths 0.5-0.25-0.5 cm, respectively (i.e., 14 leaves of width 0.5 cm, 32 leaves of width 0.25 cm, and 14 leaves of width 0.5 cm). The SDL leaves have a 10-40-10 pattern of widths 1.0-0.5-1.0 cm, respectively, where all widths are measured at isocenter. These MLC configurations are illustrated in FIGS. 1 and 2 and the relative size differences between the HDL MLCs and the SDL MLCs are shown.

Data objects extracted from the HDL plan include the positions of the MLC leaves and the control point MU meterset weights. The leaf positions determine the apertures at control points in the VMAT plan and the control point meterset weights determine the relative dose deposited by an individual control point within a VMAT arc. FIG. 2 presents an illustration of the method by which leaves from the HDL are adapted to the SDL. High-definition leaf positions are averaged two-by-two, and the resulting value is assigned to a corresponding leaf in the SDL MLC. Matched leaves of equal width have their positions mapped directly to the SDL MLC. A comparison of identical control points is shown in FIG. 3; the original is on the left and the adapted control point is on the right, where the result of the averaging/mapping step is seen.

Behavior of MLC Leaf Velocities Under Averaging

At the time that the original VMAT plan was created by the TPS, the optimization step included applying an MLC leaf-speed constraint to the leaves that defined potential aperture sets. Let an individual leaf's maximum travel speed between adjacent control points be C (leaf speed constraint is the same for both linacs). A simple calculation shows that this constraint will also be satisfied by any leaf in the adapted plan (i.e., after the averaging process). Let $x_1$ and $x_2$ be the positions of two adjacent HDL leaves that are averaged to provide, z, the position of an SDL leaf:

$$\vec{x} = \frac{\vec{x_1} + \vec{x_2}}{2}. \tag{1}$$

The average velocity of this leaf is then, $$\vec{v} = \frac{d\vec{x}}{dt} = \frac{1}{2}\left(\frac{d\vec{x_1}}{dt} + \frac{d\vec{x_2}}{dt}\right) = \frac{\vec{v_1} + \vec{v_2}}{2}. \tag{2}$$

Since each HDL leaf obeys the maximum-speed constraint, $$\begin{cases} |\vec{v_1}| < C \\ |\vec{v_2}| < C \end{cases} \tag{3}$$

and, by the triangle inequality, $$|\vec{v_1} + \vec{v_2}| \leq |\vec{v_1}| + |\vec{v_2}|. \tag{4}$$

Therefore, $$\vec{v} = \frac{|\vec{v_1} + \vec{v_2}|}{2} \leq \frac{|\vec{v_1}| + |\vec{v_2}|}{2} < \frac{C+C}{2} = C, \tag{5}$$

i.e., the SDL leaf also obeys the maximum-speed constraint.

In practice, some adjustments were required by the TPS upon importing the adapted plans. In a subset of patients, some adjustment of one or two leaves was required in a portion of the control points, e.g., a dialog opened in the software with a statement such as "leaf 51, in control points 34-79." Most plans adapted without any adjustment; for plans where it was necessary to accept adjustment, the position corrections suggested by the TPS were on the order of the dosimetric leaf gap, e.g., <0.15 mm and were accepted by the user in these cases.

Results

Changes to the Dose to Structures

The dose to the patient structures in the adapted SDL plans was calculated in the TPS using the Eclipse AAA algorithm and compared via DVH analysis to the corresponding structure doses in the original HDL plan. The percent difference between HDL and SDL doses (maximum and mean) to individual planning structures were calculated via $$\% \; diff = \frac{D_{SDL} - D_{HDL}}{D_{HDL}} \tag{6}$$

where $D_{SDL}$ is the mean or maximum dose to a structure in the SDL plan and $D_{HDL}$ is the corresponding dose in the original HDL plan. The homogeneity index, HI, was calculated for target structures using $$HI = \frac{D_{MAX} - D_{MIN}}{D_{MEAN}}. \tag{7}$$

Figure 5:
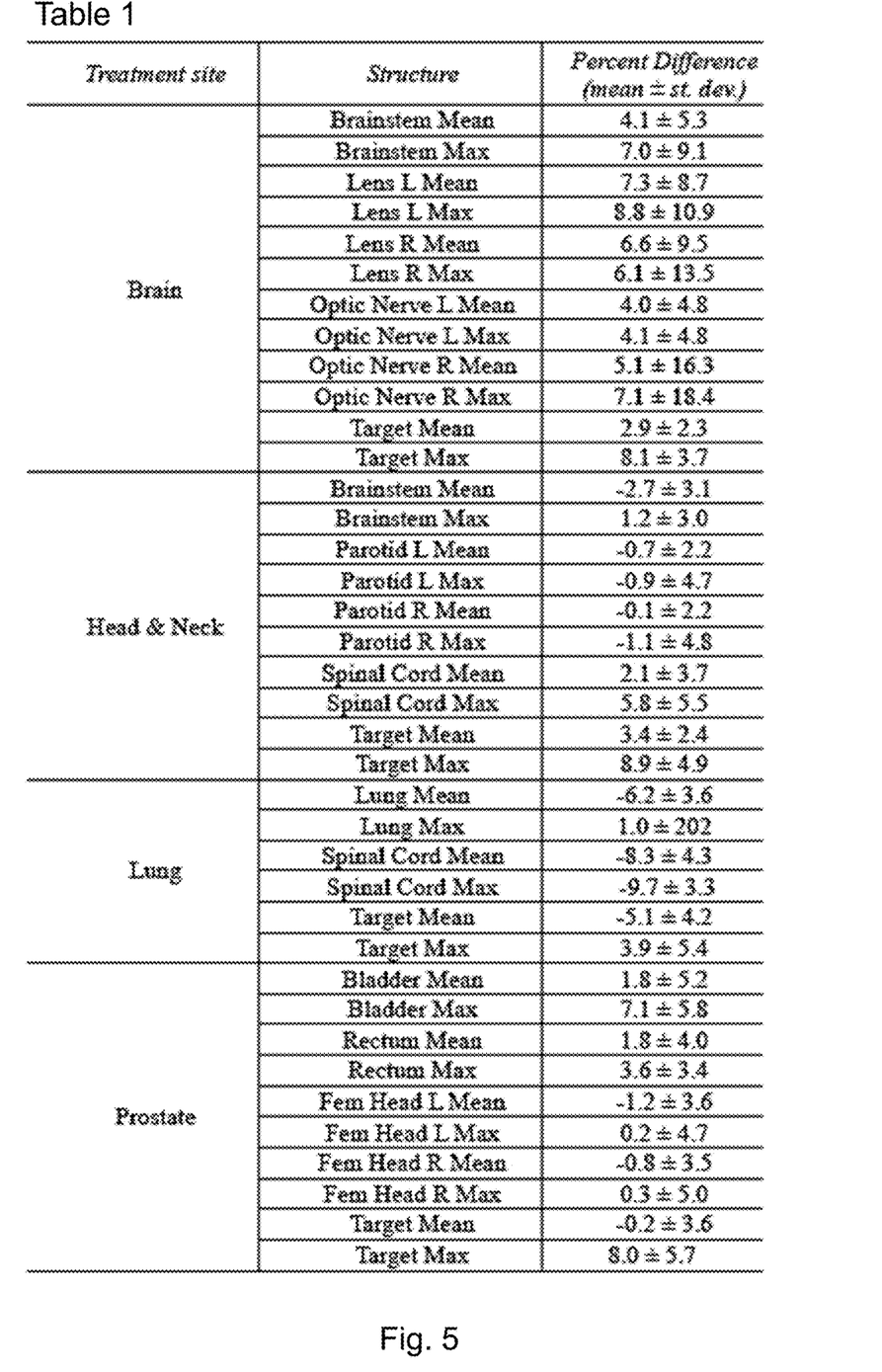
FIG. 5 (Table 1) shows mean percent differences for the target and organs-at-risk for four sets of treatment sites.

FIG. 5 (Table 1) shows the mean percent difference (Eq. 6) in maximum dose and mean dose between the HDL and the SDL planning structures for four general treatment sites (number of patients in parentheses): brain (13), head & neck (5), lung (4), and prostate (11). After discussing the results of the exemplary adaptation method, the relevant clinical group established a cutoff of ±10% as a threshold that will trigger review of the adapted DVHs. As such, no review of the adapted fraction of treatment is required for plans where the 10% threshold is not violated by any structures. FIGS. 4A-4D shows the mean percent difference for maximum and mean structure doses were ±10% for all structures analyzed. DVHs from HDL and SDL single-fraction plans for a prostate and a brain case are in FIGS. 8 and 9. Increased dose to the target structures (black line, HDL; dashed lines, SDL) can be seen as well as rightward shifts in dose in the adapted plan.

Figure 7:
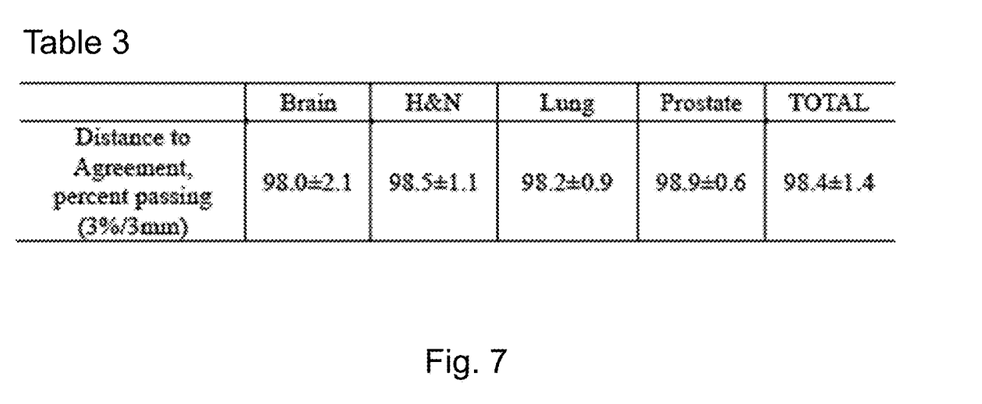
FIG. 7 (Table 3) shows pass rates for verification plans measured with the Sun Nuclear ArcCHECK® device.

Standard VMAT quality assurance measurements were performed using the ArcCHECK® device (Sun Nuclear, Melbourne, Fla.) to verify that the adapted plans were deliverable on the SDL. Verification plans were prepared for the ArcCHECK® phantom in the TPS using the adapted SDL plans. Since the present method involves making changes to the patient treatment plan directly, the delivery of a verification plan ensures that the plans defined in the adapted DICOM files are deliverable on the SDL after the adaptation method is applied. Results were compared using Sun Nuclear SNCPatient™ software package where a distance-to-agreement ("DTA") analysis was performed between the exported dose-to-phantom and the measured dose delivery on the SDL. The passing rates for the verification plan deliveries using DTA 3%/3 mm are in FIG. 7 (Table 3). The high passing rates (mean=98.4±1.4%) verify that the dose deposited in the phantom, which results from the adapted leaf aperture set, is delivered by the linac accurately and that it matches the theoretical dose calculated in the TPS.

Summation Plan

Figure 10:
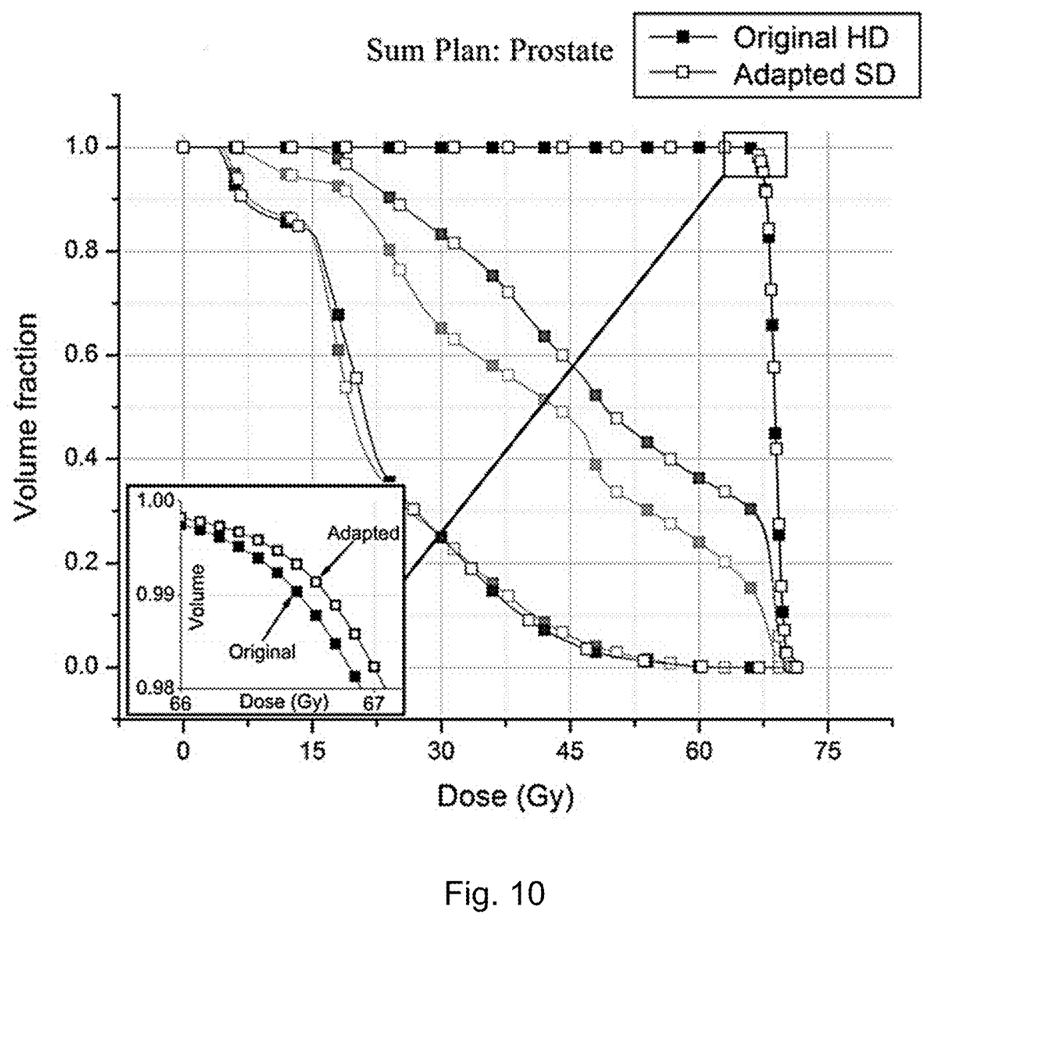
FIG. 10 shows a plan sum for a prostate treatment, wherein one fraction out of the entire course of treatment was adapted from the high-definition linac to a standard definition linac.

The purpose of the adaptation method is to develop a deliverable plan for one fraction of a treatment course in order to maintain the patient's treatment schedule during linac unavailability (e.g., downtime). The patient will most likely receive the remainder of their fractions of treatment on the original HDL machine. The results of a planning summation (one adapted plan with the remaining fractions composed of the HDL plan) for one patient are shown in FIG. 10, which shows the effect of the incorporation of the adapted fraction into the entire course of treatment. In this representative case (FIG. 10) a regular course of treatment of 1.8 Gy×25 fractions followed by several boost courses had one fraction from the 25-fraction course adapted and replaced in the summation plan. The detail of the target structure's shoulder region (lower left corner of FIG. 10 shows a slight increase in the target structure's DVH in the adapted plan.

Clinical Timeline

Figure 11:
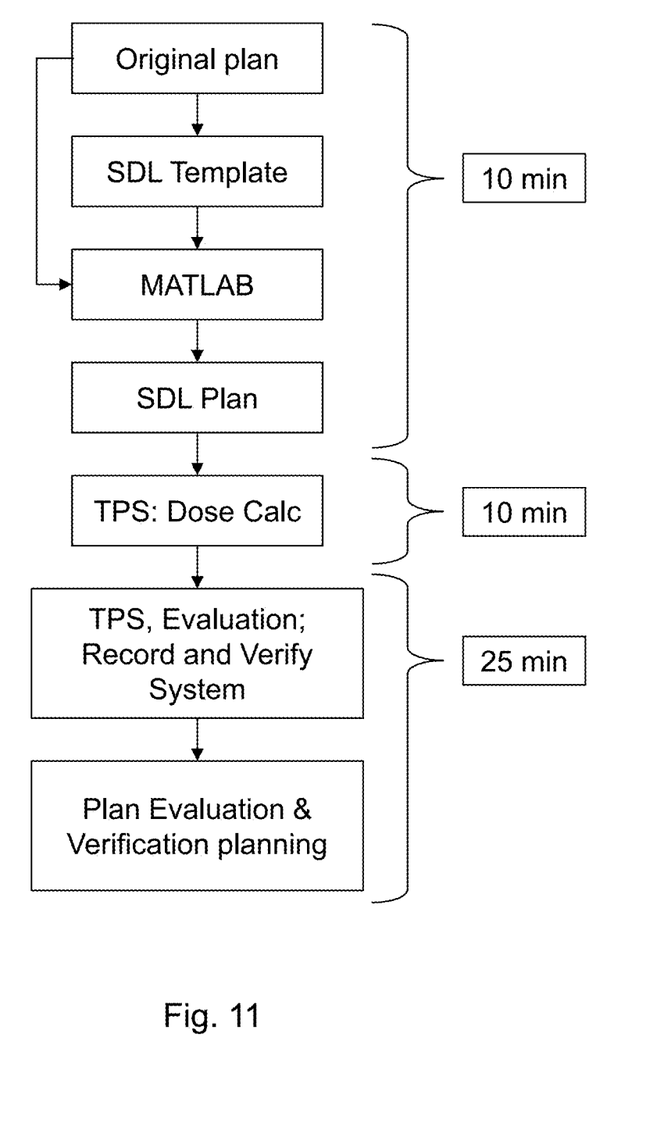
FIG. 11 is a flowchart showing the clinical timeline for adapting a VMAT plan from the high-definition linac to the standard-definition linac (adapted plan)—dose calculation will vary for individual Eclipse users; the time shown here is based on information from an exemplary clinic.

The intention of creating an adapted plan for an SDL is to allow a patient to continue treatment on the same day he/she was originally scheduled when the originally planned linac is down. The adapted plans need to be processed in the TPS and evaluated using DVH analysis and verified using phantom measurements in an efficient manner. The time required to complete the adaptation tasks (flowchart, FIG. 11) was studied. It was found that preparing an adapted fraction can be performed within 40 minutes from end-to-end, that is, from the time that physics staff is notified of the desire to proceed with a treatment on a different linac to the evaluation of the verification plan delivery on the SDL. If an adapted plan is rejected for dosimetric reasons, the clinic pays a temporal cost of approximately 20 minutes since the plan will not be verified using phantom measurements.

The average time for individual tasks was quantified while adapting the set of HDL plans used in the exemplary study. Most of the work involved the use of the TPS and was performed at a computing station with the exception of the delivery of the verification plans. The timeline in FIG. 11 outlines the general components involved in VMAT plan adaptation for a single patient with typical times noted. Some economy of scale will allow for adaptation tasks to be completed in parallel, i.e., multiple physicists may work in tandem to process multiple patient plans.

Figure 8:
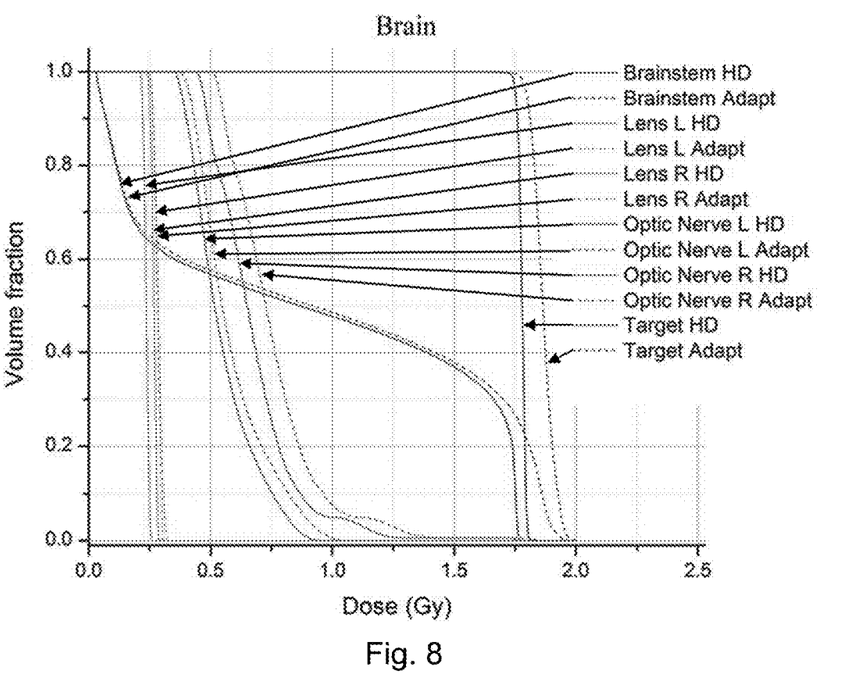
FIG. 8 shows dose volume histograms ("DVHs") of one brain patient, where the original planned DVHs are solid and the adapted plan is shown with dashed lines (the expected rightward shifts are seen as averaging of the high-definition leaves leads to degradation to the original conformity of the MLC leaves in the case of the Target, and the loss of shielding in the case of organs-at-risk)
Figure 9:
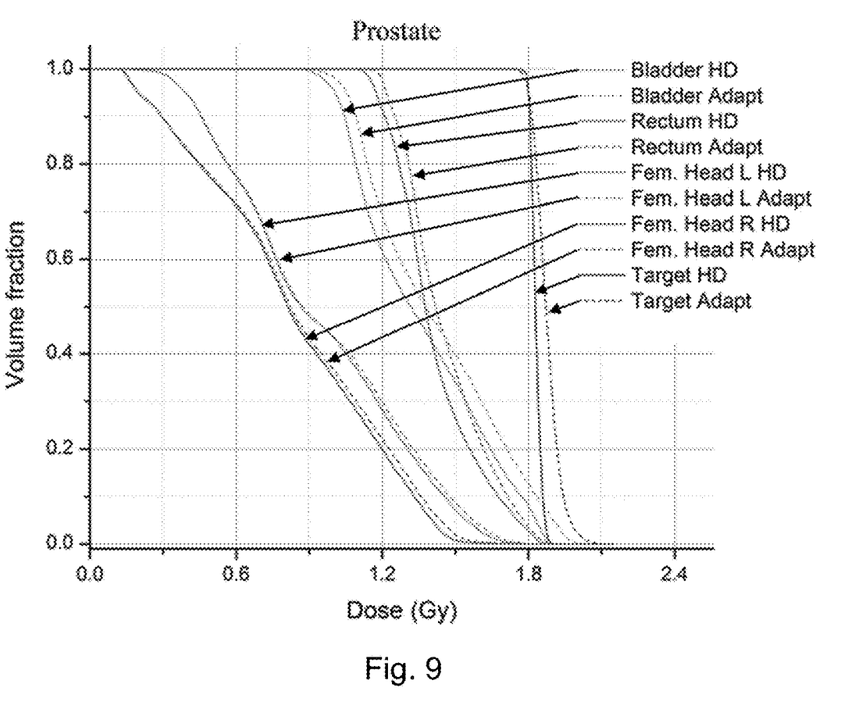
FIG. 9 shows DVHs of one prostate patient, where the original planned DVHs are solid and the adapted plan is shown with dashed lines.

DVH behavior, FIGS. 8 and 9, shows the adapted plan structures shifting toward higher dose. Since the MLC aperture set from the original TPS plan was the result of an optimization process. The leaf averaging process creates a modified MLC aperture set that is an approximation of the original solution and is most probably not at a minimum according to the objective function score. Recall, however, that an objective of this work was to develop a process where re-optimization is not performed but, nevertheless, results in an effective plan that can be safely delivered for a limited number of fractions.

DISCUSSION

Dose Changes

Figure 6:
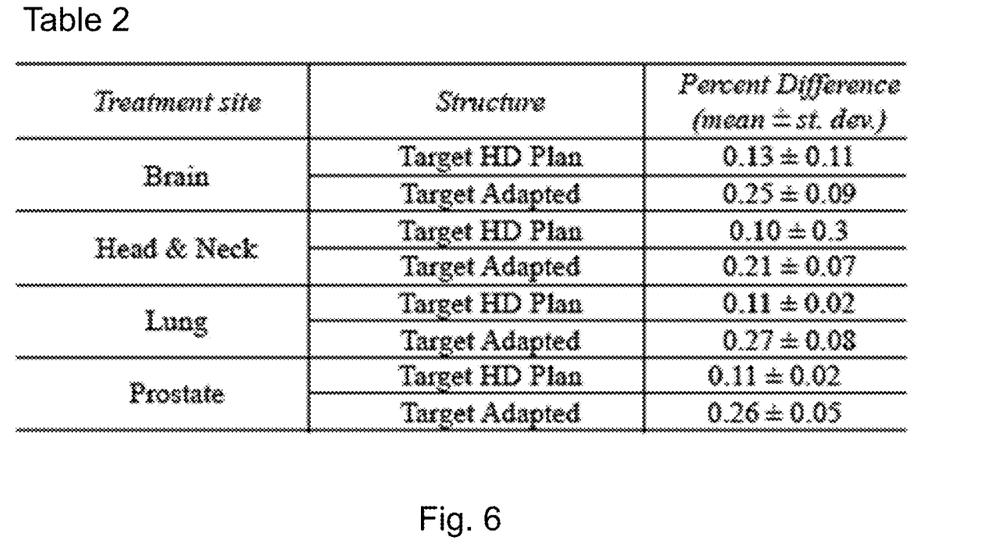
FIG. 6 (Table 2) shows the homogeneity indices of the original HD plans and their corresponding standard-definition adapted plans.

Changes in the maximum, mean, and minimum dose to structures between HDL and SDL plans were observed (FIG. 5 (Table 1). Rightward shifts in DVHs of the OARS in the adapted, single-fraction, plans are shown in FIGS. 8 and 9. Recalling that with the averaging method for adapting HDL MLC leaves in the central region of the HD120 (the 64, 0.25 cm width, leaves), the rightward shifts in OAR DVHs were interpreted as evidence of the removal of shielding of the OARs by MLCs. In terms of leaf positions, the averaging technique must lead to more areas of exposure of the OARs in the beams-eye-view which results in migration of the corresponding structure DVHs to the right. A parallel to the OAR-exposure effect is seen in the target DVH where leaf averaging reduces the conformance to the target as evidenced by the changes in H I values (FIG. 6 (Table 2)). Looking at the target DVH for an adapted plan, an increase in the size of the tail region was observed. This part of the target DVH characterizes a subset of the total voxels contained within the target structure. This voxel population receives more dose in the adapted plan than in the original. Since the adapted plan is normalized according to a prescribed dose in the same manner as the original HDL plan, the tail can be interpreted as the increase in the relative dose between the voxels represented by the tail portion to the remaining voxels in the structure. The effect of the adapted fraction on the entire course of treatment is small (detail window, lower left corner of FIG. 10) compared to the original HDL-only dose (a complete course of treatment with no adapted fraction). Therefore, a patient functionally receives his/her full course of treatment with the incorporation of a single adapted fraction while maintaining the original schedule of treatment.

Patient treatment outcomes are correlated to treatment schedules, and since the plan in summation is nearly equivalent to the original HDL-only plan, there is assurance that the patient is treated as if the originally planned linac was always available. This opens up the possibility of transferring the patient from an HDL to an SDL, thereby avoiding interruption to the patient treatment schedule and any indeterminate radiobiological effects due to the interruption of the fractionation schedule.

Clinical Cases

Prostate treatments make up a large proportion of the VMAT treatments on the exemplary HDL, and most candidates for linac transfer will be prostate treatments. The mean dose to the rectum in prostate cases increased by 1.8±4.0% with maximum target dose increasing 8.0±5.7% in adapted plans showing that prostate tended to adapt well to the SDL adaptation vs. the typical adapted brain plan. In brain cases, changes to optic nerve mean and maximum doses ranged much higher with adapted Optic Nerve R increasing 7.1±18.4%. The spread in mean and maximum dose to structures for prostate (FIG. 4D) is much smaller than for brain (FIG. 4A) over the set of all structures. This implies that the averaging technique used in the present method leads to less degradation of the original prostate plan compared to the adapted prostate plan.

From the perspective of VMAT plan optimization, the averaging method creates a plan, were there to be access to the objective function (scoring function) within the Eclipse VMAT optimizer, that would presumably resolve to a less optimal score, with adapted prostate plans losing less score value than brain plans on average.

Head-and-neck (H&N) cases (FIG. 4B) performed well after adaptation with mean percent differences varying over a smaller range compared to Lung and Brain cases. Since the variance (red bars) extends over a smaller range compared to other treatment sites, a larger proportion of the population of adapted Head-and-neck plans will not violate the ±10% dose deviation policy, compared to brain and lung plans. This tighter variance demonstrates a kind of stability in adapted H&N VMAT plans that is especially apparent when comparing to brain. Mean percent dose in prostate cases also showed similar stability to those of H&N. Lung cases (FIG. 4C) displayed good variance, relative to brain, but less so compared to H&N and prostate.

Clinical Application and Timing

The exemplary clinic has a large proportion of VMAT case on the HDL. In one two-week period 51.7% of the cases treated on the HDL were VMAT. During a period of HDL downtime, there could be more than ten patients who are potential linac transfer candidates. Let one assume that re-planning of the patient treatments for the SDL will take at least two hours each. With two members of clinic staff working solely on the re-planning tasks, verification planning deliveries would commence after at least 10 work-hours. Considering the ten-patient example, treatments would commence after an estimated 12.00 hours (assuming two physicists performing verification planning and delivery at a cost of 25 minutes per patient plan). The present method allows the preparation of 10 adapted plans in 1.67 hours (with two staff members) leading to a total of 5.42 hours of time between the beginning of HDL-to-SDL adaptation until the completion of verification plan delivery.

Although the present disclosure has been described with respect to one or more particular embodiments, it will be understood that other embodiments of the present disclosure may be made without departing from the spirit and scope of the present disclosure.

We claim:

1. A computer-implemented method of adapting a volumetric modulated arc therapy ("VMAT") plan for a linac having a high-definition multileaf collimator ("HDL MLC") for use with a linac having a standard-definition MLC ("SDL MLC"), the method comprising:
   extracting a set of HDL MLC leaf positions corresponding to a set of control points of the VMAT plan from an HDL DICOM file;
   mapping each leaf of a plurality of leaves of the SDL MLC to one or more leaves of a plurality of leaves of the HDL MLC according to a width of each leaf of the SDL MLC and HDL MLC;
   for each control point of the VMAT plan, determining a leaf position of each leaf of the SDL MLC based on an average leaf position(s) of the corresponding mapped leaves of the HDL MLC to create an adapted plan;
   saving the adapted plan to an electronic file in DICOM format.

2. The method of claim 1, further comprising constraining a velocity of each leaf of the SDL MLC during movement between adjacent control points of the adapted plan.

3. The method of claim 1, further comprising calculating a dose to a patient structure; and comparing the calculated dose to a dose to the patient structure of the VMAT plan.

4. The method of claim 3, wherein comparing the calculated dose to a dose of the VMAT plan includes calculating a homogeneity index.

5. The method of claim 1, further comprising operating a linac according to the adapted plan.

6. A non-transitory computer-readable storage medium having stored thereon processor-executable software instructions configured to cause a processor to perform operations comprising:
   extracting a set of HDL MLC leaf positions corresponding to a set of control points of a VMAT plan from an HDL DICOM file;
   mapping each leaf of a plurality of leaves of the SDL MLC to one or more leaves of a plurality of leaves of the HDL MLC according to a width of each leaf of the SDL MLC and HDL MLC;
   for each control point of the VMAT plan, determining a leaf position of each leaf of the SDL MLC based on an average leaf position(s) of the corresponding mapped leaves of the HDL MLC to create an adapted plan;
   saving the adapted plan to an electronic file in DICOM format.

7. The computer-readable storage medium of claim 6, further having instructions comprising constraining a velocity of each leaf of the SDL MLC during movement between adjacent control points of the adapted plan.

8. The computer-readable storage medium of claim 6, further having instructions comprising calculating a dose to a patient structure; and comparing the calculated dose to a dose to the patient structure of the VMAT plan.

9. The computer-readable storage medium of claim 8, wherein comparing the calculated dose to a dose of the VMAT plan includes calculating a homogeneity index.

10. A system for operating a linac, comprising:
    a processor;
    an electronic storage device in communication with the processor; and
    a linac having a standard-definition multileaf collimator ("SDL MLC") in communication with the processor;
    wherein the processor is programmed to:
      extract a set of HDL MLC leaf positions corresponding to a set of control points of a VMAT plan from an HDL DICOM file;
      map each leaf of a plurality of leaves of the SDL MLC to one or more leaves of a plurality of leaves of an HDL MLC according to a width of each leaf of the SDL MLC and HDL MLC;
      for each control point of the VMAT plan, determining a leaf position of each leaf of the SDL MLC based on an average leaf position(s) of the corresponding mapped leaves of the HDL MLC to create an adapted plan; and
    operate the SDL MLC according to the adapted plan.

11. The method of claim 2, further comprising operating a linac according to the adapted plan.

12. The method of claim 3, further comprising operating a linac according to the adapted plan.

13. The method of claim 4, further comprising operating a linac according to the adapted plan.

* * * * *